US006503761B1

(12) United States Patent
Koenig et al.

(10) Patent No.: US 6,503,761 B1
(45) Date of Patent: *Jan. 7, 2003

(54) SELECTIVE REMOVAL OF CONTAMINANTS FROM A SURFACE USING ARTICLES HAVING MAGNETS

(75) Inventors: David W. Koenig, Menasha; Brenda M. Nelson; Beth Anne Lange, both of Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,472

(22) Filed: Oct. 19, 1999

(51) Int. Cl.$^7$ .............................................. G01N 33/335
(52) U.S. Cl. ..................... 436/526; 436/518; 436/530; 436/531; 436/532; 436/533; 436/538; 436/541; 436/72; 436/73; 436/806; 424/484; 424/489; 424/490; 424/443; 424/447; 424/449; 424/9.8; 435/7.1; 435/7.2; 435/7.4; 435/7.32; 435/30; 435/32; 435/34; 428/283
(58) Field of Search ................................. 436/526, 518, 436/530, 531–533, 538, 541, 72, 73, 806; 424/484, 489, 490, 443, 447, 449, 9.8; 435/7.1, 7.2, 7.4, 7.32, 30, 32, 34; 600/15; 428/283, 36.1

(56) References Cited

U.S. PATENT DOCUMENTS

| | | | |
|---|---|---|---|
| 3,970,518 A | * 7/1976 | Giaever | 23/230 |
| 4,201,827 A | * 5/1980 | Heitkamp | 428/283 |
| 4,225,580 A | * 9/1980 | Rothman et al. | 424/78 |
| 4,230,685 A | * 10/1980 | Senyei et al. | 424/12 |
| 4,452,773 A | * 6/1984 | Molday | 424/1.1 |
| 4,537,767 A | * 8/1985 | Rothman et al. | 424/78 |
| 4,672,040 A | 6/1987 | Josephson | |
| 4,677,055 A | * 6/1987 | Dodin et al. | 435/7 |
| 4,677,067 A | * 6/1987 | Schwartz et al. | 435/177 |
| 4,873,102 A | 10/1989 | Chang et al. | |
| 4,965,007 A | 10/1990 | Yudelson | |
| 5,000,203 A | 3/1991 | Hamada | |
| 5,160,725 A | 11/1992 | Pilgrimm | 424/9 |
| 5,187,209 A | * 2/1993 | Hirai et al. | 523/205 |
| 5,415,997 A | 5/1995 | Atrache et al. | |
| 5,445,971 A | * 8/1995 | Rohr | 436/526 |
| 5,468,529 A | * 11/1995 | Kwon et al. | 428/36.1 |
| 5,492,754 A | * 2/1996 | Chen | 428/284 |
| 5,516,531 A | 5/1996 | Makino et al. | |
| 5,518,890 A | * 5/1996 | Starkweather et al. | 435/7.94 |
| 5,536,644 A | 7/1996 | Ullman et al. | |
| 5,576,185 A | * 11/1996 | Coulter et al. | 435/7.23 |
| 5,607,667 A | * 3/1997 | Holcomb | 424/70.1 |
| 5,637,165 A | * 6/1997 | Chen | 156/62.2 |
| 5,658,583 A | 8/1997 | Zhang et al. | |
| 5,665,582 A | 9/1997 | Kausch et al. | |
| 5,695,946 A | 12/1997 | Benjamin et al. | |
| 5,741,336 A | 4/1998 | Fraser | |
| 5,800,835 A | 9/1998 | Zastrow et al. | 424/647 |
| 6,027,945 A | * 2/2000 | Smith | 436/501 |
| 6,066,673 A | * 5/2000 | McIver et al. | 514/634 |
| 6,107,261 A | * 8/2000 | Taylor et al. | 510/131 |
| 6,126,588 A | * 10/2000 | Flamant et al. | 600/15 |
| 6,136,549 A | * 10/2000 | Feistel | 435/7.1 |
| 6,146,324 A | * 11/2000 | Engel | 600/15 |

FOREIGN PATENT DOCUMENTS

| | | | |
|---|---|---|---|
| DE | 36 29 761 | 3/1987 | .......... A45D/27/26 |
| FR | 2 268 512 | 11/1975 | ............ A61K/7/00 |
| FR | 2 400 883 | 3/1979 | ........... A61B/17/52 |
| JP | 3019948 | 1/1999 | |

OTHER PUBLICATIONS

John A. Oberteuffer; "Magnetic Separation: A Review of Principles, Devices, and Applications"; *IEEE Transactions on Magnetics*, vol. MAG–10, No. 2, Jun. 1974; pp. 223–238.

Hancock et al.; "A rapid and highly selective approach to cell separations using an immunomagnetic colloid"; *Journal of Immunological Methods*; 164 (1993); pp. 51–60.

Gupta et al.; "Magnetically Controlled Targeted Micro–Carrier Systems"; *Life Sciences*; vol. 44; No. 3; 1989; pp. 175–186.

Safarik et al.; "The application of magnetic separations in applied microbiology"; *Journal of Applied Bacteriology*; 1995; 78; pp. 575–585.

Widder et al.; "Specific Cell Binding Using Staphylococcal Protein A Magnetic Microspheres"; *Journal of Pharmaceutical Sciences*; vol. 70, No. 4; Apr. 1981; pp. 387–389.

Vaccaro et al.; "Use of Monoclonal Antibodies with Magnetic Particles to Separate Cell Subpopulations by Positive Selection"; *Methods in Molecular Biology*; vol. 45: Monoclonal Antibody Protocols; pp. 253–259.

Rye et al.; "Immunobead Filtration: A Novel Approach for the Isolation and Propagation of Tumor Cells"; *American Journal of Pathology*; vol. 150, No. 1; Jan. 1997.

Pope et al.; "Evaluation of magnetic alginate beads as a solid support for positive selection of CD34+ cells"; *Journal of Biomedical Materials Research* vol. 28, (1994) pp. 449–457.

(List continued on next page.)

Primary Examiner—Christopher L. Chin
Assistant Examiner—Pensee T. Do
(74) Attorney, Agent, or Firm—Pauley Petersen Kinne & Erickson

(57) ABSTRACT

A system and method for removing contaminants from a surface. The system is designed to use particles having means thereon which are capable of selectively binding to a contaminant or contaminants of interest. The particles are applied to the surface whereupon the contaminants bind to the particle. When the particle is removed, the desired contaminants are also removed. Preferably, the present invention utilizes magnetic particles having iron therein. The particles may then be readily removed using magnets. The means for binding the contaminant to the particle preferably comprise a ligand or a charge specifically designed to remove the contaminant of interest. The particles may be included in a carrier to facilitate their application to the surface. The invention is especially useful for the removal of contaminants from skin.

61 Claims, 2 Drawing Sheets

OTHER PUBLICATIONS

J. Kandzia et al.; "Cell Separation: Comparison Between Magnetic Immuno–Microspheres (MIMS) and FACS"; Proceedings of the International Meeting, Rostock, German Democratic Republic, Sep. 24–28,1984; *Cell Electrophoresis*; 1985; pp.87–93.

M. Markiewicz et al.; Immunomagnetic Method of CD34(+) Cell Separation; *Transplantation Proceedings*; vol. 28, No. 6; Dec. 1996; pp. 3526–3527.

Per Arne Risoen et al.; One–Step Magnetic Purification of Recombinant DNA–Binding Proteins Using Magnetizable Phosphocellulose; *Protein Expression and Purification*; vol. 6, No. 3, Jun. 1995; pp. 272–277.

A.I. Autenshlyus et al.; Magnetic–sensitive dextran–ferrite immunosorbents (for diagnostic and therapy); *Journal of Magnetism and Magnetic Materials*; vol. 122, Nos. 1–3; Apr. 1993; pp. 360–363.

A.M.A. Carneiro Leao et al.; "Immobilization of Protein on Ferromagnetic Dacron"; *Applied Biochemistry and Biotechnology*; vol. 31, ISSN: 0173–2289; 1991; pp. 53–58.

J.E. Davies et al.; "A Comparison of the Use of Two Immunomagnetic Microspheres for Secondary Purification of Pancreatic Islets"; *Transplantation*; vol. 62, No. 9, Nov. 15, 1996; pp. 1301–1306.

R. Alan Hardwick et al.; "Design of Large–Scale Separation Systems for Positive and Negative Immunomagnetic Selection of Cells Using Superparamagnetic Microspheres"; *Journal of Hematotherapy*; vol. I, No. 4, Winter 1992.

Anders Hedrum et al.; "Immunomagnetic Recovery of *Chlamydia trachomatis* from Urine with Subsequent Colorimetric DNA Detection"; *PCR Methods an dApplications*; vol. 2, No. 2, Nov. 1992; pp. 167–171.

Heidi A. Israel; "Immunomagnetic separation: A tool for microbiology"; *American Biotechnology Laboratory*; vol. 12., No. 6, May 1994; pp. 50 and 52.

Sumner Levine; "Magnetic Techniques for in vitro Isolation of Leucocytes"; *Science*, vol. 123, No. 3184; Jan. 6, 1956; pp. 185–186.

Xiaohong Li et al.; "Synthesis of Magnetic Polymer Microspheres and Application for Immobilization of Proteinase of *Balillus sublitis*"; *Journal of Applied Polymer Science*; vol. 58, No. 11, Dec. 12, 19951 pp. 1991–1997.

Leonid B. Margolis et al.; "Magnetoliposomes: Another Principle of Cell Sorting"; *Biochimica Et Biophysica Acta* (International Journal of Biochemistry and Biophysics); 1983; pp. 193–195.

Tadashi Matsunaga et al.; "Chemiluminescence Enzyme Immunoassay Using Bacterial Magnetic Particles"; *Analytical Chemistry* vol. 68, No. 20, Oct. 15, 1996; pp. 3551–3554.

Noriyuki Nakamura et al.; "Detection and Removal of *Escherichia coli* Using Fluorescein Isothiocyanate Conjugated Monoclonal Antibody Immobilized on Bacterial Magnetic Particles"; *Analytical Chemistry*, vol. 65, No. 15; Aug. 1, 1993; pp. 2036–2039.

P. Ndhlovu et al.; "Optimization of the Magnetic Bead Antigen Capture Enzyme Immuno Assay for the detection of circulating anodic antigens in mixed Schistosoma infections"; *Acta Tropica*, vol. 59, issue 3, (1995) pp. 223–235.

J. Plavins et al.; "Study of colloidal magnetite–binding erythrocytes: Prospects for cell separation"; *Journal of Magnetism and Magnetic Materials*, vol. 122, Nos. 1–3, Apr. 1993; pp. 349–353.

Patrick M. Regan et al.; "Development fo a nucleic acid capture probe with reverse transcriptase–polymerase chain reaction to detect poliovirus in groundwater"; *Journal of Virological Methods*, vol. 64, 1997; pp. 65–72.

J.G. Treleaven et al.; "Removal of Neuroblastoma Cells from Bone Marrow with Monoclonal Antibodies Conjugated to Magnetic Microspheres"; *The Lancet*, Jan. 14, 1984; pp. 70–73.

Mirka Safarikova et al.; "Magneticke Separace V Prirodnich Vedach A Biotechnologiich"; *Chemicke listy* 5; 1995; pp. 269–336 (No Translation Available).

Dennis E. Vaccaro, "Applications of magnetic separation: Cell sorting"; *American Biotechnology Laboratory*; vol. 8, No. 5, Apr. 1990; pp. 3030, 32–35.

\* cited by examiner

SELECTIVE REMOVAL OF CONTAMINANTS FROM A SURFACE USING ARTICLES HAVING MAGNETS

FIELD OF THE INVENTION

The present invention is directed to a system and method whereby contaminants may be selectively removed from skin. In particular, the present invention is directed to a system and method which uses particles having a degree of magnetism wherein the particles are constructed and arranged to remove particular contaminants, such as microbial contaminants and debris, further wherein the particles and the contaminants are then removed from the skin using articles containing magnets.

BACKGROUND OF THE INVENTION

Humans have vast amounts of debris and microbes existing in their bodily fluids and on their skin. Many of the microbes are beneficial to the health and well-being of the individual. However, many of these microbes are contaminants which are not beneficial. Many of these non-beneficial microbes exist in body fluids which contact the skin, such as tears, perspiration, oils, nasal secretions, and bodily waste. The microbes may also exist in wounds. These microbes, along with debris contaminants, may irritate the skin causing a variety of skin problems such as rashes, breakouts, clogged pores, or discoloration of the skin or, with wounds, slow down the rate at which the wound will heal.

Many different products have been produced to help eliminate the problems associated with debris and the non-beneficial microbes. Different cleaning products are used which include detergents. These detergents effectively remove excess oils and fluids, thereby reducing the number of both beneficial and non-beneficial microbes. However, the non-beneficial microbes still exist on the skin, just in lower numbers. Additionally, if too much oil is removed from the skin, then dryness of the skin could result.

Other products have introduced microbiocides which are effective at killing all microbes on the skin. However, since these microbiocides eliminate beneficial microbes as well as non-beneficial microbes, these products destroy beneficial skin ecology and thus have a negative impact on skin health.

Accordingly, what is needed is a system and method of removing debris and non-beneficial microbes from skin without removing beneficial microbes to help reduce the skin problems associated with the non-beneficial microbes while maintaining skin health.

SUMMARY OF THE INVENTION

The present invention is directed to a system and method of removing microbial contaminants from skin. The system utilizes receptor materials which selectively bind to the microbe or microbes of interest. The receptor materials are placed on the surface of the skin wherein they attach to and bind the microbes. Then, the receptor material and bound microbes are removed from the skin. This allows non-beneficial microbes to be removed while beneficial microbes remain, thereby maintaining skin health or expediting the healing of wounds.

The system preferably includes the use of particles onto which the receptor materials are placed. These particles are designed to be placed on the skin wherein the receptor materials may bind to the desired microbes. Then, means are provided which remove the particles and the accompanying receptor material and microbes from the surface of the skin.

Preferably, the present invention utilizes particles which have a magnetic charge. Then, after these magnetic particles are used to remove the microbes, articles having magnets contained therein or thereon may be used to remove the magnetic particles from the skin.

Accordingly, it is an object of the present invention to provide a system which can selectively attach and remove desired microbes.

It is another object of the present invention to provide a system which maintains skin health by removing non-beneficial microbes while permitting beneficial microbes to remain on the skin.

It is still another object of the present invention to provide a system which removes non-beneficial microbes while not drying or otherwise damaging the skin.

It is still another object of the present invention to provide a system which utilizes magnetic particles and magnets to aid in the selective removal of the non-beneficial microbes.

It is still another object of the present invention to provide a method of removing non-beneficial microbes from skin.

It is still another object of the present invention to provide a method of removing non-beneficial microbes by utilizing particles which selectively bind to the non-beneficial microbes on the skin and, upon removal of the particles, carry off the non-beneficial microbes.

It is still another object of the present invention to provide a method of removing non-beneficial microbes by utilizing magnetic particles and magnets.

The present invention can also be used with a multitude of different personal care items such as diapers, tissues, feminine products, wipes, bandages, and cleansing materials.

These and other objects and advantages of the present invention will become apparent after a review of the following detailed description of the disclosed embodiments.

DETAILED DESCRIPTION

Figure 1:
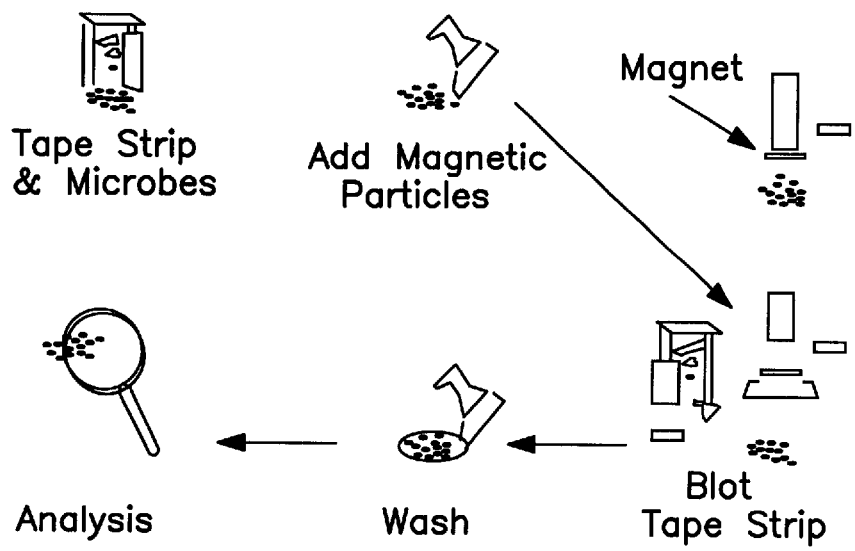
FIG. 1 outlines the test procedure by which an embodiment of the present invention was used to determine the effectiveness of the magnetic test strips.

The present invention is directed to a system and method for removing contaminants from skin. The system may be used to remove a wide range of contaminants such as debris or microbes. The system preferably utilizes ligands which bind to the contaminant of interest. Then, the ligands and the bound contaminants are removed leaving desirable microbes to maintain skin health.

The ligands are associated with particulate materials which are applied to the skin whereupon the ligand or charge can bind to the contaminant of interest. Then, means are provided which remove the particulate material. In the preferred embodiment of the present invention, the particulate materials have a magnetic charge, and these magnetic particles are removed through the use of an article having magnets contained therein or thereon. Depending on the desired use, these magnets may be located within a personal care product. Preferably, the system employs reactive superparamagnetic monodispersed microspheres (SMM) that are coated with ligands to specifically bind the target microbes.

Alternatively, instead of attaching a ligand, the magnetic particles may be either positively or negatively charged to thereby attract and bind other desired microbes and contaminants. The charge may be given to the particle by at least two methods. One would be to use material that already has the appropriate charge. For example, cellulose could be used to impart an overall negative charge to the particle. Conversely, chitin could be used to impart an overall positive charge to the particle. The second method would be to modify the materials by chemical means to change the charge characteristics of the surface. For example, addition of amines would impart a positive charge; addition of carboxyl groups a negative charge.

Native silanol groups on the surface of silica microspheres are readily reacted with aqueous or solvent-based silane coupling agents to yield preactivated silica microspheres with a large variety of surface functional groups. Examples include chloromethyl, carboxyl, and amino groups. Oligonucleotides can be covalently bound to surface-modified silica via the 5'-amino end. Lipids can be bound via the carboxyl group on the fatty acid chain and propylamine surface groups on the silica.

The present invention also includes methods of removing contaminants from skin by applying particles having the ability to selectively bind to a contaminant or contaminants of interest. Then, the particles are removed from the skin to clear away the undesirable contaminants. By "selectively bind" is meant that the particles can adhere to certain intended contaminants and not adhere to certain other non-intended materials.

In the preferred embodiment, the present invention utilizes magnetic particles. Preferably, these magnetic particles comprise a particle containing iron. Preferably, the particle is non-toxic and is capable of binding a ligand thereto. Particles useful in the present invention include those made from natural polymers, random copolymers, or plastics. Representative examples include natural polymers such as cellulose; random copolymers such as polybutylene copolymer, polyethylene, polypropylene copolymers, polyethylene elastomers; and plastics such as polystyrene, polyethylene, polypropylene, rayon, nylon, polyvinylidine chloride, and polyesters, chitin, starch, dextran and modified-starch. Silica could be used as an inorganic carrier. Other inorganic carriers might include clays. The type of particle used will vary depending several considerations, including the intended use or the contaminant to be removed. However, in general, natural polymers, such as cellulose, impregnated with iron are the preferred type of particle.

The size of the particle may also vary depending on the intended use or the product in which the particle is to be used. However, if the particle is too large, it may aggravate the skin as it is applied. Therefore, in general, the preferred particles are smaller in size. Preferably, the particles are less than about 25 µm in diameter. More preferably, the particles are from about 3–4 µm in diameter.

The amount of iron contained within each particle will vary depending on the amount of charge desired, the overall size of the particle, the carrier within which the particles will be applied to the skin, if any, and the location and number of magnets used to remove the particle. However, in general, the particles will comprise from about 1% to about 25% by weight of iron. More preferably, the particles will comprise from about 10% to about 20% by weight of iron. This will result in the particle having a magnetic mass susceptibility of from about 50,000,000 to about 200,000,000 m$^3$/kg.

Once the desired particle type, size and iron content have been selected, then the particle may be modified to either attach a ligand thereto or charged to obtain the desired polarity. As discussed previously, the choice between a ligand or ligands and a charge will depend upon the type of contaminant to be removed and will affect the composition of the particle. If a charge is used, the charge may either be a positive charge or a negative charge. If a ligand is used, it may be selected from a wide variety of useful ligands.

A positively charged particle is capable of being used to remove yeast and bacteria (negatively charged) and any negatively charged molecule. Examples of particles useful as positively charged particles include, but are not limited to, chitin, diethylaminoethyl, ciethyl[2-hydroxypropyl] aminoethyl, polyethyleneimine, triethylaminohydroxypropyl, quaternary ammonium, quaternary alkylamine, quaternary alkylanolamine, trimethylbenzylammonium, dimethylethanolbenzylammonium, polyamine, alkylamine, dimethylethanolamine, octadecyldimethyltrimethoxylsilpropylammonium chloride, and kymene.

A negatively charged molecule may be used to remove protein and other biological contaminates, not including yeast or bacteria. Examples of particles useful as negatively charged particles include, but are not limited to, carboxymethyl cellulose, sulfopropyl cellulose, cellulose phosphate, DOWEX®, DUOLITE®, AMBERLITE®, and bentonite.

A large number of ligands may be used in the present invention. These ligands include plant lectins and antibodies among others. Furthermore, extracts of plants and natural products may also be used.

Plant lectins useful in the present invention include, but are not limited to, lentil lectin, wheat germ lectin, *dolichos biflorus, galanthus nivalis, glycine max, heli pomatia, lens culinaris, phaseolus vulgaris, phytolacca americana, ulex europaeus*, and *vicia villosa*. These lectins are useful at removing microbial materials, and especially any cells with mannopyranosyl or glucopyranosyl residues on the membrane surface. They may also help in the removal of proteins or skin debris with similar characteristics. Other microbes which may be removed include those having glucose, mannose, or n-acetyl-glucosaminyl residues in the microbes cell wall and other skin debris material.

Other ligands which may be used include *dolichos biflorus, galanthus nivalis, glycine max, heli pomatia, lens culinaris, phaseolus vulgaris, phytolacca americana, ulex europaeus, and vicia villosa.*

Antibodies useful in the present invention include those having specific antibodies for any microbe associated cell wall or membrane component. Other ligands useful in the present invention include those that use cell surface receptors specific for microbes. These include, but are not limited to, Staphylococcus, Steptococcus, Candida, and Propionibacterium. All of these are specific for cell surface receptors which bind glycosides. Those glycosides could be attached to the magnetic particle.

If a ligand is used as the means for removing the contaminant, then the ligand must be attached to the particle such that when the particle is applied to the skin, the ligand is able to bind with the contaminant or contaminants of choice and remove these contaminants when the particle is removed from the skin. There are a plurality of known methods which may be used to attach the ligand to the particle. However, the preferred methods for the present invention include direct adsorption and covalent attachment.

Direct adsorption involves adsorbing the ligand onto the surface of the particle. Simply adsorbing protein, especially polyclonal IgG, on the surface of polystyrene microspheres is successful more than 95% of the time. For maximum surface coverage (up to a monolayer), buffer pH should be at, or slightly more basic than, IgG's isoelectric point (that is, pH 8), where the protein is in its most relaxed, compact form. Tris buffer (pH 8.0) and phosphate buffer (pH 7.4) work well. The Fc and Fab portions of IgG adsorb differently in response to pH changes. A slightly alkaline pH optimizes adsorption of the Fc portion and ensures relative suppression of Fab adsorption.

As an alternative to simple adsorption, IgG and serum albumin (human or bovine) can be mixed and then adsorbed simultaneously. One commercial protocol calls for a weight ratio of 1 IgG to 10 albumin in the coadsorption mixture. Adsorption can be followed by glutaraldehyde cross-linking of the mixed proteins on the microsphere surface.

In covalent bonding, the ligand is covalently bonded to the particle. For example, haptens and other low-molecular-weight labels, which on their own might not adsorb well or remain attached, can be covalently bound to proteins (such as BSA), dextran, polylysine, or other polymers that adsorb well. Another alternative is to adsorb the polymer on the particles and then couple the hapten or other label. These polyhaptens are used commercially. Another embodiment is to adsorb peptide onto the microspheres and then covalently link more peptide onto the surface.

Also, any polyclonal antibody (PoAb) may also be used, such as those from mouse, goat, rabbit, pig, or bovine. These polyclonal antibodies adsorb well and attach to microspheres to form generic microspheres. These then capture any of several poorly adsorbing monoclonal antibodies (MoAb). In theory, a manufacturer can make a series of tests (or assays) from one PoAb preparation.

Some evidence indicates that one can attach 10–40% more protein covalently than by adsorption. When the desired protein coverage is low, covalent coupling may provide more-precise control of the coating level. Covalent coupling binds protein more securely, an asset in production of tests or assays that are so sensitive that they would be influenced by minute quantities of IgG that might leach off the particles over time. The covalent bond is more thermally stable.

Native silanol groups on the surface of silica microspheres are readily reacted with aqueous or solvent-based silane coupling agents to yield preactivated silica microspheres with a large variety of surface functional groups. Examples include chloromethyl, carboxyl, and amino groups. DNA and RNA are isolated from serum by adsorption onto silica in the presence of chaotropic agents. Oligonucleotides can be covalently bound to surface-modified silica via the 5-amino end. Lipids can be bound via the carboxyl group on the fatty acid chain and propylamine surface groups on the silica.

After the particles have been charged or attached with a ligand, they are then ready to be applied to the skin to remove contaminants therefrom. While the particles may be applied directly to the skin, it is preferred that they be included with a carrier designed to aid the application of the particles to the skin while reducing the number of particles needed to effectively remove the desired contaminants. The carrier may be any means that permit the effective distribution of the particles over the desired area of the skin. These carriers include, but are not limited to, lotions, creams, sprays, or solutions. Other natural carriers may be used, such as alginate or chitosan. Additionally, the particles may be applied using a non-magnetic, cellulosic or polymeric wipe which is wiped across the surface of the skin.

The amount of particles added to the carrier will depend on several factors including the carrier used, the contaminants to be removed and the amount of contaminants, among others. In general, from about 0.001 to about 10 mg of particles will be included per milliliter of carrier. More preferably, the amount of particles will be from about 0.1 to about 1.0 mg/ml.

As previously discussed, the present invention preferably uses magnetic particles. Magnetic particles are used such that they may be easily removed through the use of magnets. The magnets are associated with a product, such as a personal care item. The manner in which the particles are applied to the surface and the type of product used to remove the particles will vary, depending on the contaminant to be removed and the surface area to be treated.

The magnets used in the present invention are selected so as to be incorporated into the personal care product such that they are still capable of removing the magnetic particles. The magnets may be incorporated into both woven and non-woven materials, depending on the product. Additionally, the woven and non-woven materials may be composed of natural or synthetic fibers, or a mixture of both. For example, in one embodiment, the magnets may be incorporated into facial tissues, which comprise plant fiber. In another embodiment, the magnets may be incorporated into a non-woven fabric, such as a diaper or a wipe. However, since these two embodiments result in different contact of the product with the skin, the products must be designed accordingly. For facial tissues, the magnets will come into close contact with the skin. Therefore, the number, size and/or strength of the magnets will be different when compared to magnets placed inside a diaper, which do not directly contact the skin, yet must still be able to remove magnetic particles which may have been incorporated into lotion or powder applied before the diaper was put on.

The present invention also includes methods of removing contaminants using the system of the present invention. While it is expected that the system is capable of removing contaminants, such as debris or microbes, from a skin surface, it is also contemplated that the mechanisms described below may also permit the system to be used to remove contaminants from a wide variety of surfaces including, but not limited to, skin, floors, windows, pets, automobiles, watercraft, and counter tops.

In use, means for removing the contaminant are associated with a particle. As previously discussed, these means may involve the attachment of a ligand or generating a charge on the particle. After the means for removing the contaminant are associated with the particle, the particle is then applied to the surface. The particles may either be applied directly, such as using a wipe, or may be included in a carrier which is applied to the surface. After the particles have been applied, the contaminants to be removed bind to the means for removing the contaminant. Then, the particles are removed from the surface using means for accomplishing the same. When the particle is removed from the surface the contaminant is also removed.

This invention is further illustrated by the following embodiments, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

In one embodiment, the magnetic particles may be placed in a carrier, such as a cream, lotion, spray or solution, and applied to an open wound. These particles could be associated with a ligand capable of removing bacteria from the wound. Then, the magnetic particles could be located in the gauze or bandage which is wrapped around the wound. Once the bandage contacted the wound, the magnets would pull the magnetic particles and contaminants from the wound. In a similar manner, the particles may be associated with a charge or another ligand and used to treat a variety of different rashes or infections.

In another embodiment, the magnetic particles may be associated with a ligand or charge that is capable of binding to microbes existing in bodily wastes. Then, the particles may be applied to, for example, a baby using a baby wipe, powder or lotion. The particles would bind with the microbes. Then, a diaper having magnets contained therein may be placed on the baby, wherein the magnets would remove the magnetic particles and contaminants from the skin of the baby, helping to prevent rashes. Similar embodiments may be used with feminine articles or adult incontinence devices.

In still another embodiment, the particles may be used to help clear pores and prevent breakouts of the skin. The particles would be associated with a ligand or charge that is capable of binding to debris or microbes existing on the skin surface. The particles may be included in a carrier such as a cream or lotion. Then, the particles are applied to the skin surface whereupon they bind with the debris or microbes. Then, an adhesive strip having magnets contained therein may be applied to the skin. When the strip is removed, the magnetic particles and contaminants would also be removed, helping to clear pores. Alternatively, a facial wipe may be used in lieu of the adhesive strip.

In still another embodiment, the particles may be used to relieve the symptoms associated with sinus problems. Irritation of the skin around the nose may be associated with microbes in the mucous. To remove these microbes, particles having the necessary ligand or charge may be applied to the nose using a carrier such as cream, lotion, or facial tissue. Then, the particles and the microbes bound thereto may be removed using another facial tissue having magnets contained therein.

As can be seen, the particles of the present invention may be used in many different embodiments depending upon the contaminant to be removed, the surface being treated, the carrier used, and the means for removing the particles and contaminants. It should be understood, of course, that the foregoing embodiments relate only to some of the preferred embodiments of the present invention and that numerous modifications or alterations may be made therein without departing from the spirit and the scope of the invention as set forth in the appended claims.

EXAMPLES

In the Examples, ex-vivo skin test strips were prepared. These strips were then used to determine the effectiveness of the present invention at removing *C. albicans* or *E. coli* from skin. FIG. 1 outlines the magnetic removal protocol used for these Examples. The Examples were performed as follows:

Procedure:
1. Make tape strips, 5 pulls per tape strip on forearm.
2. Place tape strips in wells of 6 well plate.
3. Block with 2.0 ml 5% Bovine Serum Albumin (BSA) in Phosphate Buffered Saline (PBS), pH 7.2.
4. Incubate 30–32 ° C., 100 RPM, 1 hr.
5. Aspirate wells of 6 well plate dry.
6. Wash tape strip with Tris Buffered Saline (TBS pH) 7.4+0.5% BSA, holding tape strip with tweezers, use eye-dropper to flush tape strip twice.
7. Add 1.0 ml ($10^6$ CFU/ml) *C. albicans* or *E. coli* in TBS pH 7.4 to each well.
8. Add 1.0 ml Typtic Soy Broth (TSB) to each well.
9. Incubate 30–32° C., 100 RPM, 1 hr.
10. Aspirate wells of 6 well plate dry.
11. Wash tape strip with TBS pH 7.4+0.5% BSA, holding tape strip with tweezers, use eye-dropper to flush tape strip twice.
12. Add 2.0 ml 1/200 Rabbit anti-*C. albicans*-Horseradish, Peroxidase (HRP) or Rabbit anti- *E.coli*-HRP in TBS pH 7.4+0.5% BSA.
13. Incubate 28–30° C., 100 RPM, 1 hr.
14. Add 2.0 ml 1/200 Sheep anti-rabbit-paramagnetic bead in TBS pH 7.4+0.5% BSA.
15. Incubate 28–30° C., 100 RPM, 1 hr.
16. Wash tape strip with TBS pH 7.4+0.5% BSA, holding tape strip with tweezers, use eye-dropper to flush tape strip twice.
17. Place tape strip in new 6 well plate.
18. Place magnet on surface of tape strip.
19. Remove magnet after 3.0 min.
20. Wash tape strip with TBS pH 7.4, holding tape strip with tweezers, use eye-dropper to flush tape strip twice.
21. Place tape strip in new 6 well plate.
22. Add 2.0 ml peroxidase substrate (ABTS).
23. Incubate 28–30° C., 100 RPM, 15–30 min, read absorbency at 405 nm.
24. Alternative measure of *C. albicans* is to fix the tape strip with 2.5% Gluteraldhye after step 11.
25. Wash tape strip with TBS pH 7.4, holding tape strip with tweezers, use eyedropper to flush tape strip twice.
26. Stain with Calcoflour white.
27. Visually enumerate yeast using fluorescent microscope.

Table 1 outlines the effectiveness of the present invention at magnetically removing *C. albicans* attached to skin.

TABLE 1

| Treatment of Skin with Attached Yeast | HRP Activity ABS 405 nm | % Removal of HRP Activity |
|---|---|---|
| No Treatment | 1.055 | |
| No Treatment | 0.844 | |
| Plastic Film | 0.802 | 15.5 |
| Magnet Covered with Plastic Film | 0.350 | 63.2 |

Figure 2:
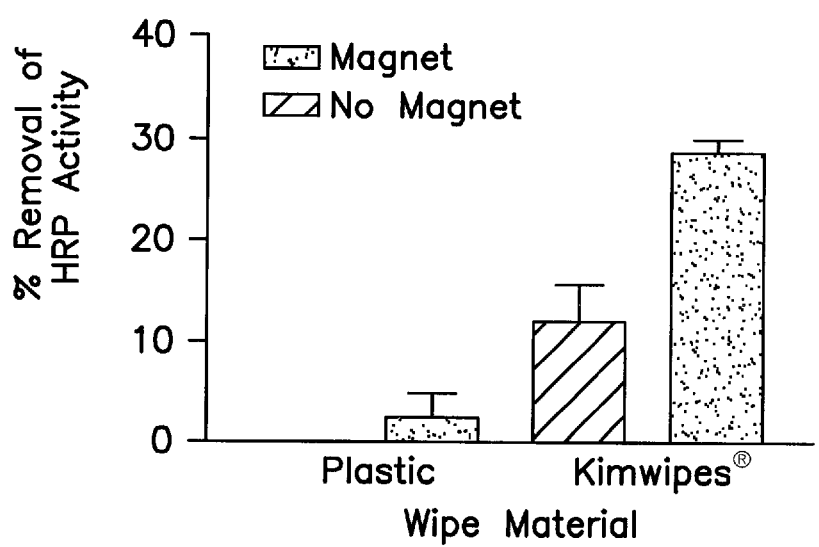
FIG. 2 is a graphical representation of the effectiveness of the present invention at removing E. coli attached to skin.
Figure 3:
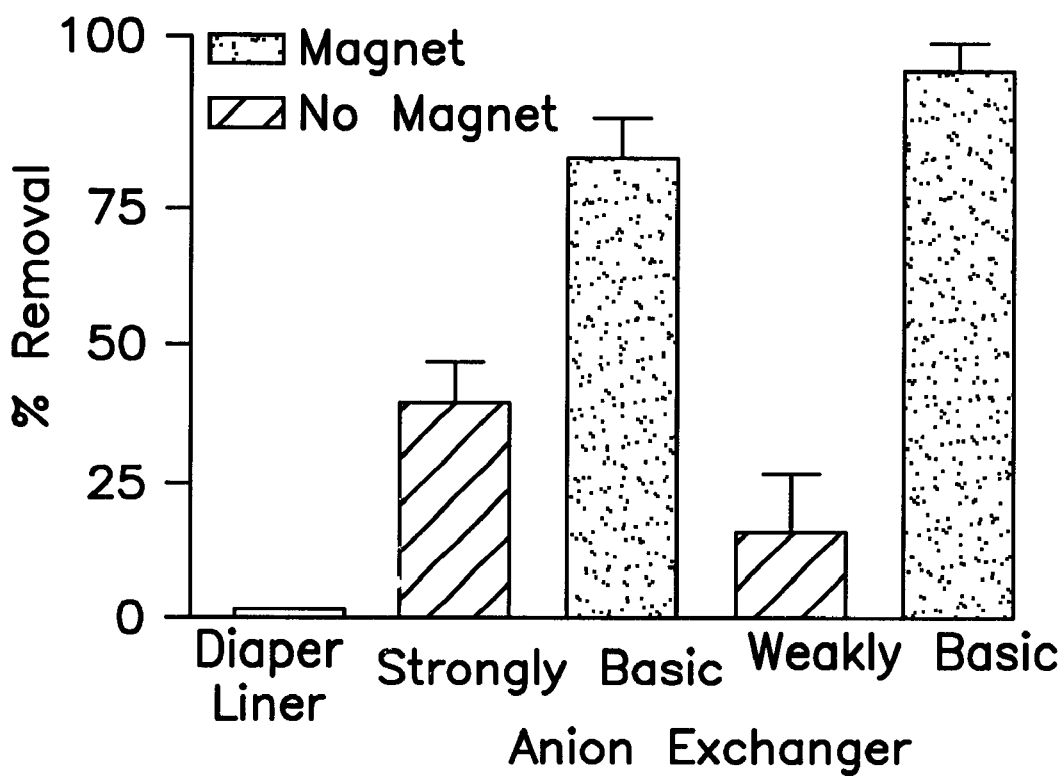
FIG. 3 a graphical representation of the effectiveness of the present invention at removing C. albicans from skin using Magnetic Cellulose Particles.

FIGS. 2 and 3 show the effectiveness of the present invention at removing *E. coli* and *C. albicans* respectively. As can be seen, the use of the magnetic particle greatly enhances the removal of contaminants from a surface such as skin.

Therefore, as these Examples indicate, the present invention offers a highly effective means for removing contaminants from a surface by utilizing a magnetic particle having means attached thereto to selectively remove the surface contaminant. Additionally, the present invention provides for methods of removing surface contaminants using these magnetic particles and means for removing the magnetic particles from the surface.

What is claimed is:

1. A system for removing a contaminant from a skin surface comprising:
   a particle having a magnetic metal element and means on the particle for selectively binding a contaminant on the skin surface;
   a carrier for applying the particle directly to the skin surface;
   a magnet; and
   a bandage having the magnet contained therein, for placing the magnet sufficiently adjacent the skin surface such that the particle and the bound contaminant can be removed from the skin surface by exposure to the magnet.

2. The system of claim 1, wherein the carrier is selected from a group consisting of a lotion, a cream, a spray, a solution, a non-magnetic cellulose wipe, a non-magnetic polymeric wipe, and combinations thereof.

3. The system of claim 2, wherein the carrier comprises about 0.001 to about 10 mg/ml of particles.

4. The system of claim 2, wherein the carrier comprises about 0.1 to about 1.0 mg/ml of particles.

5. The system of claim 1, wherein the means thereon for selectively binding a surface contaminant comprises a ligand.

6. The system of claim 5, wherein the ligand is selected from a group consisting of an antibody, a cell surface receptor, a plant lectin, dolichos biflorus, galanthus nivalis, glycine max, heli pomatia, lens culinaris, phaseolus vulgaris, phytolacca americana, ulex europaeus, vicia villosa, and combinations thereof.

7. The system of claim 1, wherein the means thereon for selectively binding a surface contaminant comprises an electrostatic interaction.

8. The system of claim 1, wherein the magnetic particle has a positive charge.

9. The system of claim 1, wherein the magnetic particle has a negative charge.

10. The system of claim 1, wherein the contaminant is selected from a group consisting of a bacteria, yeast, toxin, enzyme, debris, and combinations thereof.

11. The system of claim 1, wherein the particle has a diameter of less than about 25 $\mu$m.

12. The system of claim 1, wherein the particle has a diameter of between about 1–10 $\mu$m.

13. The system of claim 1, wherein the particle has a diameter of between about 3–4 $\mu$m.

14. The system of claim 1, wherein the magnetic metal element comprises iron and the particle comprises between about 1% to 25% by weight of iron.

15. The system of claim 1, wherein the magnetic metal element comprises iron and the particle comprises between about 10% to 20% by weight of iron.

16. A system for removing a contaminant from a skin surface comprising:
   a particle having a magnetic metal element and means on the particle for selectively binding a contaminant on the skin surface;
   a carrier for applying the particle directly to the skin surface;
   a magnet; and
   a diaper having the magnet contained therein, for placing the magnet sufficiently adjacent the skin surface such that the particle and the bound contaminant can be removed from the skin surface by exposure to the magnet.

17. The system of claim 16, wherein the carrier is selected from a group consisting of a lotion, a cream, a spray, a solution, a non-magnetic cellulose wipe, a non-magnetic polymeric wipe, and combinations thereof.

18. The system of claim 17, wherein the carrier comprises about 0.001 to about 10 mg/ml of particles.

19. The system of claim 17, wherein the carrier comprises about 0.1 to about 1.0 mg/ml of particles.

20. The system of claim 16, wherein the means thereon for selectively binding a surface contaminant comprises a ligand.

21. The system of claim 20, wherein the ligand is selected from a group consisting of an antibody, a cell surface receptor, a plant lectin, dolichos biflorus, galanthus nivalis, glycine max, heli pomatia, lens culinaris, phaseolus vulgaris, phytolacca americana, ulex europaeus, vicia villosa, and combinations thereof.

22. The system of claim 16, wherein the means thereon for selectively binding a surface contaminant comprises an electrostatic interaction.

23. The system of claim 16, wherein the magnetic particle has a positive charge.

24. The system of claim 16, wherein the magnetic particle has a negative charge.

25. The system of claim 16, wherein the contaminant is selected from a group consisting of a bacteria, yeast, toxin, enzyme, debris, and combinations thereof.

26. The system of claim 16, wherein the particle has a diameter of less than about 25 $\mu$m.

27. The system of claim 16, wherein the particle has a diameter of between about 1–10 $\mu$m.

28. The system of claim 16, wherein the particle has a diameter of between about 3–4 $\mu$m.

29. The system of claim 16, wherein the magnetic metal element comprises iron and the particle comprises between about 1% to 25% by weight of iron.

30. The system of claim 16, wherein the magnetic metal element comprises iron and the particle comprises between about 10% to 20% by weight of iron.

31. A system for removing a contaminant from a skin surface comprising:
   a particle having a magnetic metal element and means on the particle for selectively binding a contaminant on the skin surface;
   a carrier for applying the particle directly to the skin surface;
   a magnet; and
   an adhesive strip having the magnet contained therein, for placing the magnet sufficiently adjacent the skin surface such that the particle and the bound contaminant can be removed from the skin surface by exposure to the magnet.

32. The system of claim 31, wherein the carrier is selected from a group consisting of a lotion, a cream, a spray, a solution, a non-magnetic cellulose wipe, a non-magnetic polymeric wipe, and combinations thereof.

33. The system of claim 32, wherein the carrier comprises about 0.001 to about 10 mg/ml of particles.

34. The system of claim 32, wherein the carrier comprises about 0.1 to about 1.0 mg/ml of particles.

35. The system of claim 31, wherein the means thereon for selectively binding a surface contaminant comprises a ligand.

36. The system of claim 35, wherein the ligand is selected from a group consisting of an antibody, a cell surface receptor, a plant lectin, dolichos biflorus, galanthus nivalis, glycine max, heli pomatia, lens culinaris, phaseolus vulgaris, phytolacca americana, ulex europaeus, vicia villosa, and combinations thereof.

37. The system of claim 31, wherein the means thereon for selectively binding a surface contaminant comprises an electrostatic interaction.

38. The system of claim 31, wherein the magnetic particle has a positive charge.

39. The system of claim 31, wherein the magnetic particle has a negative charge.

40. The system of claim 31, wherein the contaminant is selected from a group consisting of a bacteria, yeast, toxin, enzyme, debris, and combinations thereof.

41. The system of claim 31, wherein the particle has a diameter of less than about 25 $\mu$m.

42. The system of claim 31, wherein the particle has a diameter of between about 1–10$\mu$m.

43. The system of claim 31, wherein the particle has a diameter of between about 3–4 $\mu$m.

44. The system of claim 31, wherein the magnetic metal element comprises iron and the particle comprises between about 1% to 25% by weight of iron.

45. The system of claim 31, wherein the magnetic metal element comprises iron and the particle comprises between about 10% to 20% by weight of iron.

46. A system for removing a contaminant from a skin surface comprising:
   a particle having a magnetic metal element and means on the particle for selectively binding a contaminant on the skin surface;
   a carrier for applying the particle directly to the skin surface;
   a magnet; and
   a facial tissue having the magnet contained therein, for placing the magnet sufficiently adjacent the skin surface such that the particle and the bound contaminant can be removed from the skin surface by exposure to the magnet.

47. The system of claim 46, wherein the carrier is selected from a group consisting of a lotion, a cream, a spray, a solution, a non-magnetic cellulose wipe, a non-magnetic polymeric wipe, and combinations thereof.

48. The system of claim 47, wherein the carrier comprises about 0.001 to about 10 mg/ml of particles.

49. The system of claim 47, wherein the carrier comprises about 0.1 to about 1.0 mg/ml of particles.

50. The system of claim 46, wherein the means thereon for selectively binding a surface contaminant comprises a ligand.

51. The system of claim 50, wherein the ligand is selected from a group consisting of an antibody, a cell surface receptor, a plant lectin, dolichos biflorus, galanthus nivalis, glycine max, heli pomatia, lens culinaris, phaseolus vulgaris, phytolacca americana, ulex europaeus, vicia villosa, and combinations thereof.

52. The system of claim 46, wherein the means thereon for selectively binding a surface contaminant comprises an electrostatic interaction.

53. The system of claim 46, wherein the magnetic particle has a positive charge.

54. The system of claim 46, wherein the magnetic particle has a negative charge.

55. The system of claim 46, wherein the contaminant is selected from a group consisting of a bacteria, yeast, toxin, enzyme, debris, and combinations thereof.

56. The system of claim 46, wherein the particle has a diameter of less than about 25 $\mu$m.

57. The system of claim 46, wherein the particle has a diameter of between about 1–10 $\mu$m.

58. The system of claim 46, wherein the particle has a diameter of between about 3–4 $\mu$m.

59. The system of claim 46, wherein the magnetic metal element comprises iron and the particle comprises between about 1% to 25% by weight of iron.

60. The system of claim 46, wherein the magnetic metal element comprises iron and the particle comprises between about 10% to 20% by weight of iron.

61. A system for removing a contaminant from a skin surface comprising:
   a particle having a magnetic metal element and means on the particle for selectively binding a contaminant on the skin surface;
   a carrier for applying the particle directly to the skin surface;
   a magnet; and
   an adult incontinence device having the magnet contained therein, for placing the magnet sufficiently adjacent the skin surface such that the particle and the bound contaminant can be removed from the skin surface by exposure to the magnet.

* * * * *